(12) United States Patent
Jackson et al.

(10) Patent No.: US 12,070,348 B2
(45) Date of Patent: Aug. 27, 2024

(54) METHODS AND SYSTEMS FOR COMPUTED TOMOGRAPHY

(71) Applicant: GE Precision Healthcare LLC, Wauwatosa, WI (US)

(72) Inventors: John Irvin Jackson, Brookfield, WI (US); Mark Edward Woodford, Waukesha, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 0 days.

(21) Appl. No.: 18/087,626

(22) Filed: Dec. 22, 2022

(65) Prior Publication Data

US 2023/0130015 A1 Apr. 27, 2023

Related U.S. Application Data

(62) Division of application No. 15/441,962, filed on Feb. 24, 2017, now Pat. No. 11,559,272.

(51) Int. Cl.
*A61B 6/00* (2006.01)
*A61B 6/03* (2006.01)
*A61B 6/50* (2024.01)
*A61B 5/00* (2006.01)
*A61B 5/349* (2021.01)

(52) U.S. Cl.
CPC ............ *A61B 6/5205* (2013.01); *A61B 6/032* (2013.01); *A61B 6/503* (2013.01); *A61B 6/5211* (2013.01); *A61B 6/5288* (2013.01); *A61B 5/349* (2021.01); *A61B 5/7292* (2013.01); *A61B 6/481* (2013.01); *A61B 6/486* (2013.01); *A61B 6/507* (2013.01)

(58) Field of Classification Search
CPC ....... A61B 6/5205; A61B 6/032; A61B 6/503; A61B 6/5211; A61B 6/5288; A61B 5/349; A61B 5/7292; A61B 6/481; A61B 6/486; A61B 6/507; G16H 50/20
See application file for complete search history.

(56) References Cited

U.S. PATENT DOCUMENTS

| | | | | |
|---|---|---|---|---|
| 6,266,553 | B1 * | 7/2001 | Fluhrer | A61B 6/032 600/509 |
| 2007/0293771 | A1 * | 12/2007 | Noren | A61N 1/36514 600/481 |
| 2015/0243070 | A1 * | 8/2015 | Ra | A61B 6/5217 382/131 |

OTHER PUBLICATIONS

Boudoulas et al (Linear Relationship Between Electrical Systole, Mechanical Systole, and Heart Rate, Chest, vol. 80, Issue 5, Nov. 1981, pp. 613-617) (Year: 1981).*

* cited by examiner

*Primary Examiner* — Alexei Bykhovski

(57) ABSTRACT

Methods and systems are provided for cardiac computed tomography imaging. In one embodiment, a method comprises reconstructing an image from projection data acquired during a scan with a reconstruction time determined based on a model relating a timing of an event to be imaged to a heart rate measured during the scan. In this way, the timing of a reconstruction may be consistently applied for a series of reconstructions, thereby inherently registering the reconstructions.

7 Claims, 4 Drawing Sheets

METHODS AND SYSTEMS FOR COMPUTED TOMOGRAPHY

CROSS-REFERENCE TO RELATED APPLICATIONS

This application is a divisional of U.S. application Ser. No. 15/441,962, filed on Feb. 24, 2017, the disclosure of which is incorporated herein by reference in its entirety.

FIELD

Embodiments of the subject matter disclosed herein relate to non-invasive diagnostic imaging, and more particularly, to image reconstruction for cardiac computed tomography (CT) imaging systems.

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of x-rays through the target volume, to acquire image data and to construct tomographic images (e.g., three-dimensional representations of the interior of the human body or of other imaged structures).

Dynamic perfusion of the heart, liver, or other organs requires that images be generated over a period of time as a contrast agent moves through the organ. Analysis of the variation in the localized contrast agent is then used to infer any of a number of perfusion metrics, such as the blood flow, volume, or mean transit time. The analysis requires that the same portion of anatomy be analyzed at a series of time points. Displacements in the anatomy from image to image or volume to volume will introduce errors and reduce the accuracy of the perfusion analysis.

BRIEF DESCRIPTION

In one embodiment, a method comprises reconstructing an image from projection data acquired during a scan with a reconstruction time determined based on a model relating a timing of an event to be imaged to a heart rate measured during the scan. In this way, the timing of a reconstruction may be consistently applied for a series of reconstructions, thereby inherently registering the reconstructions.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
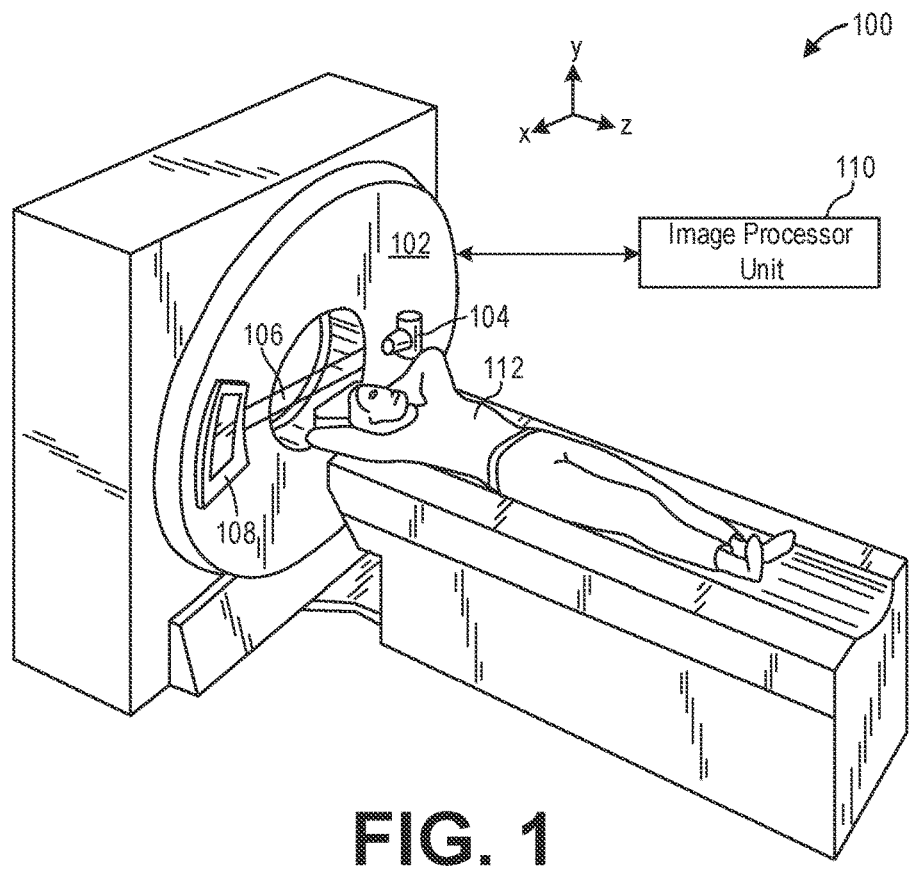
FIG. 1 shows a pictorial view of an imaging system according to an embodiment of the invention.

The following description relates to various embodiments of medical imaging system. In particular, methods and systems are provided for imaging an organ such as a heart with an imaging system, such as the CT imaging system depicted in FIGS. 1 and 2. A method for consistently imaging an organ, such as the method depicted in FIG. 3 and illustrated in FIG. 4, may include dynamically determining a reconstruction time for a series of reconstructions so that the reconstructions are best registered. Additionally, a method for obtaining consistent image reconstructions in the presence of irregular heartbeats, such as the method depicted in FIG. 5, may include reconstructing multiple images from data acquired during the irregular cardiac cycle, and selecting the image that best registers with neighboring frames.

Though a CT system is described by way of example, it should be understood that the present techniques may also be useful when applied to images acquired using other imaging modalities, such as tomosynthesis, C-arm angiography, and so forth. The present discussion of a CT imaging modality is provided merely as an example of one suitable imaging modality.

As used herein, the term "pixel" also includes embodiments of the invention where the data is represented by a "voxel." Thus, both the terms "pixel" and "voxel" may be used interchangeably herein.

As used herein, the phrase "reconstructing an image" is not intended to exclude embodiments of the present invention in which data representing an image is generated, but a viewable image is not. Therefore, as used herein, the term "image" broadly refers to both viewable images and data representing a viewable image. However, many embodiments generate (or are configured to generate) at least one viewable image.

Various embodiments may be implemented in connection with different types of imaging systems. For example, various embodiments may be implemented in connection with a CT imaging system in which an x-ray source projects a fan- or cone-shaped beam that is collimated to lie within an x-y plane of a Cartesian coordinate system and generally referred to as an "imaging plane." The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurement from all the detectors is acquired separately to produce a transmission profile.

In third-generation CT systems, the x-ray source and the detector array are rotated with a gantry within the imaging plane and around the object to be imaged such that the angle at which the x-ray beam intersects the object constantly changes. A complete gantry rotation occurs when the gantry concludes one full 360 degree revolution. A group of x-ray attenuation measurements (e.g., projection data) from the detector array at one gantry angle is referred to as a "view." A view is, therefore, each incremental position of the gantry. A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as a filtered backprojection (FBP) technique. This process converts the attenuation measurements from a scan into integers called "CT numbers" or "Hounsfield units" (HU), which are used to control the brightness of a corresponding pixel on, for example, a cathode ray tube display.

To reduce the total scan time for long superior-inferior extent, a "helical" scan may be performed. To perform a helical scan, the patient is moved in the z direction synchronously with the rotation of the gantry, while the data for the prescribed number of slices is acquired. Such a system generates a single helix from a fan- or cone-beam helical scan. The helix mapped out by the fan- or cone beam yields projection data from which images in each prescribed slice may be reconstructed. In addition to reducing scan time, helical scanning provides other advantages such as better use of injected contrast, improved image reconstruction at arbitrary locations, and better three-dimensional images.

FIG. 1 illustrates an exemplary CT system 100 configured to allow fast and iterative image reconstruction. Particularly, the CT system 100 is configured to image a subject such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray radiation source 104 configured to project a beam of x-ray radiation 106 for use in imaging the patient. Specifically, the radiation source 104 is configured to project the x-rays 106 towards a detector array 108 positioned on the opposite side of the gantry 102. Although FIG. 1 depicts only a single radiation source 104, in certain embodiments, multiple radiation sources may be employed to project a plurality of x-rays 106 for acquiring projection data corresponding to the patient at different energy levels.

In certain embodiments, the CT system 100 further includes an image processing unit 110 configured to reconstruct images of a target volume of the patient using an iterative or analytic image reconstruction method. For example, the image processing unit 110 may use an analytic image reconstruction approach such as filtered backprojection (FBP) to reconstruct images of a target volume of the patient. As another example, the image processing unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the patient.

Figure 2:
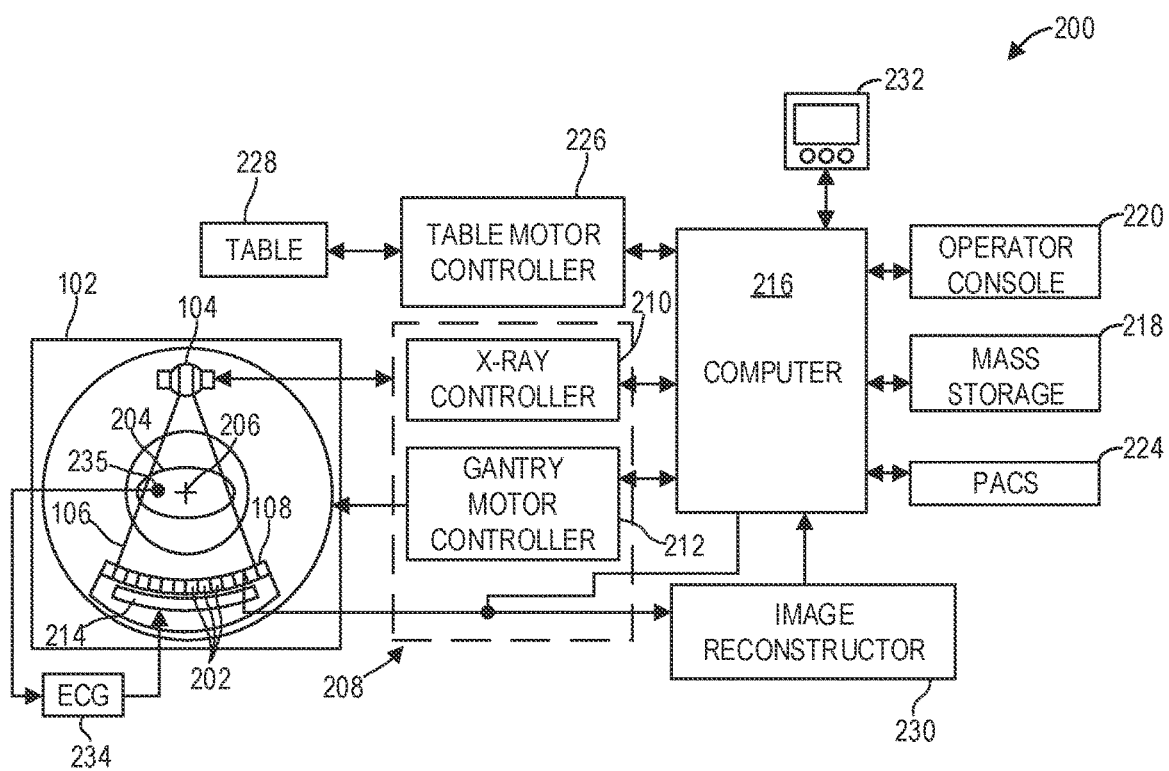
FIG. 2 shows a block schematic diagram of an exemplary imaging system according to an embodiment of the invention.

FIG. 2 illustrates an exemplary imaging system 200 similar to the CT system 100 of FIG. 1. In accordance with aspects of the present disclosure, the system 200 is configured to perform automatic exposure control. In one embodiment, the system 200 includes the detector array 108 (see FIG. 1). The detector array 108 further includes a plurality of detector elements 202 that together sense the x-ray beams 106 (see FIG. 1) that pass through a subject 204 such as a patient to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

In one embodiment, the system 200 includes a control mechanism 208 to control movement of the components such as rotation of the gantry 102 and the operation of the x-ray radiation source 104. In certain embodiments, the control mechanism 208 further includes an x-ray controller 210 configured to provide power and timing signals to the radiation source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. As described further below, DAS 214 also receives electrocardiogram (ECG) signals from an ECG monitor 234 connected to the subject 204 via leads 235 to acquire cardiac data of the subject 204. The data sampled and digitized by the DAS 214 is transmitted to a computing device (also referred to as processor) 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage device.

Additionally, the computing device 216 provides commands and parameters to one or more of the DAS 214, the x-ray controller 210, ECG monitor 234, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen, as non-limiting examples, to allow the operator to specify the commands and/or scanning parameters.

Although FIG. 2 illustrates only one operator console 220, more than one operator console may be coupled to the system 200, for example, for inputting or outputting system parameters, requesting examinations, and/or viewing images. Further, in certain embodiments, the system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the system 200 either includes, or is coupled to a picture archiving and communications system (PACS) 224. In an exemplary implementation, the PACS 224 is further coupled to a remote system such as a radiology department information system, hospital information system, and/or to an internal and/or external network (not shown) to allow operators at different locations to supply commands and parameters and/or gain access to the image data.

The computing device 216 uses the operator-supplied and/or system-defined commands and parameters to operate a table motor controller 226, which in turn, may control a motorized table 228. Particularly, the table motor controller 226 moves the table 228 for appropriately positioning the subject 204 in the gantry for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the system 200 and instead the computing device 216 may perform one or more functions of the image reconstructor 230. Moreover, the image reconstructor 230 may be located locally or remotely, and may be operatively connected to the system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Additionally or alternatively, the image reconstructor 230 transmits the reconstructed images to the computing device 216 for generating useful patient information for diagnosis and evaluation. In certain embodiments, the computing device 216 transmits the reconstructed images and/or the patient information to a display 232 communicatively coupled to the computing device 216 and/or the image reconstructor 230. In one embodiment, the display 232 allows the operator to evaluate the imaged anatomy. The display 232 may also allow the operator to select a volume of interest (VOI) and/or request patient information, for example, via a graphical user interface (GUI) for a subsequent scan or processing.

As discussed hereinabove, dynamic perfusion of the heart, liver, or other organ depends on images that are generated over a period of time as a contrast agent moves through the organ. Analysis of the variation in the localized contrast agent is then used to infer any of a number of perfusion metrics, such as blood flow, volume, or mean transit time. In the analysis, the same portion of the anatomy is analyzed at a series of time points. Displacements in the anatomy from image to image or volume to volume will introduce errors and reduce the accuracy of the analysis. In a sequence of 15 to 20 or 25 acquisitions, even one reconstruction that does not register well with the others can significantly degrade the results of the perfusion analysis. Therefore, it is desirable to have images or volumes that are well-registered. Frame to frame (image to image or volume to volume) misregistration can result from inconsistency in cardiac position from non-periodic cardiac motion, such as would be encountered with a varying heart rate. Registration, either rigid or non-rigid, can help remove the impact of these displacements, but these registration techniques are not perfect. As described further herein, improved registration methods include reconstructing images at times that generate images that are as similar as possible in registration, prior to any subsequent registration processing. Several techniques are described herein to generate images that are inherently well-registered, especially in the presence of a non-constant heart rhythm.

Figure 3:
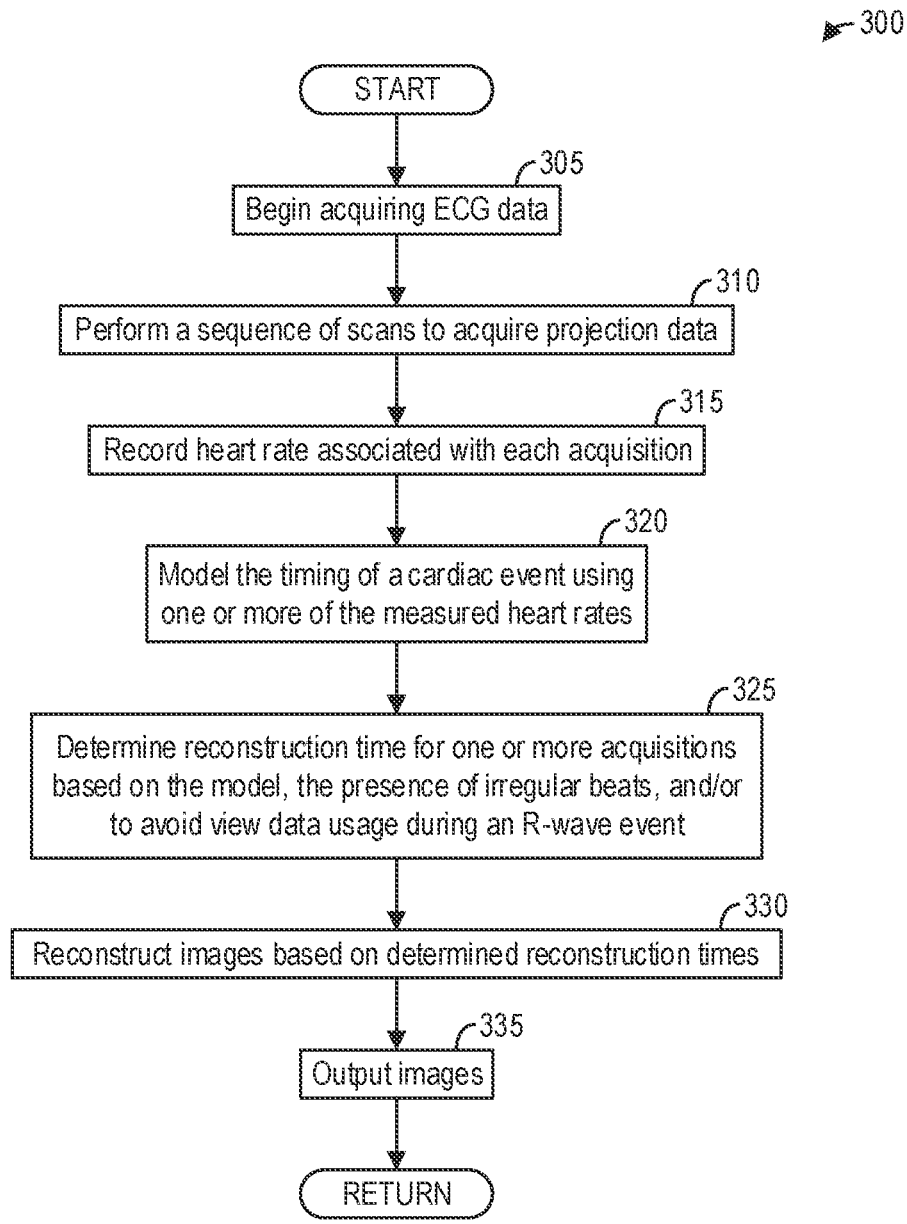
FIG. 3 shows a high-level flow chart illustrating an example method for consistently imaging an organ over time according to an embodiment of the invention.

FIG. 3 shows a high-level flow chart illustrating an example method 300 for consistently imaging an organ according to an embodiment. In particular, method 300 relates to consistently imaging a heart during a selected phase of the heart cycle for a series of acquisitions. Method 300 may be described with regard to the systems and components of FIGS. 1-2, though it should be understood that the method may be implemented with other systems and components without departing from the scope of the present disclosure. Method 300 may be implemented as executable instructions in non-transitory memory of a computing device such as computer 216.

Method 300 begins at 305. At 305, method 300 begins acquiring ECG data for a subject. For example, ECG data may be acquired via the ECG leads 235 of the ECG monitor 234 positioned on the subject 204. The ECG data or the ECG signal may be collected from the patient to synchronize the acquisition of imaging data with the quiescent period of cardiac motion.

At 310, method 300 performs a sequence of scans to acquire projection data. For example, method 300 may control the x-ray source 104 to administer x-rays to the subject 204 in the form of a fan or cone while CT projection data is acquired via the detectors 108 and the DAS 214. Method 300 may perform each scan to acquire data during a CT data acquisition window corresponding to the quiescent periods in the real-time phase of the cardiac cycle where the heart is relatively stationary.

At 315, method 300 records the heart rate associated with each acquisition. By using the ECG data, the instantaneous heart rate for each acquisition can be recorded. For example, method 300 may calculate the heart rate associated with each acquisition based on the R wave-to-R wave (RR) interval recorded by the ECG.

At 320, method 300 models the timing of a cardiac event using one or more of the measured heart rates. The model depends on the particular cardiac event selected for imaging. For example, for reconstructions targeted for the end of systole, the relationship between the heart rate and the electromechanical systole (QS2) interval may be linear. As an illustrative and non-limiting example, the QS2 interval may be related to the heart rate (HR) by $$QS2=520-2.1\ HR$$

for healthy males, with different coefficients for healthy females. Such relationships between heart rate and a cardiac event, which may comprise the electrical systole (QT) instead of QS2 in some examples, can be obtained via regression studies of patients. Thus, method 300 may model the timing of a cardiac event by inputting the recorded heart rates into a linear or in some examples non-linear equation relating the heart rate to the timing of the cardiac event.

Continuing at 325, method 300 determines the reconstruction time for one or more acquisitions based on the model, the presence of irregular heartbeats, and/or to avoid view data usage during an R-wave event. For example, the reconstruction time may be selected based on the modeled timing of the cardiac event. Further, the reconstruction time may be selected and/or adjusted based on whether the acquisition corresponds to a heartbeat with a heart rate that is irregular with respect to the average of other heart rates recorded by the ECG. For a heart rate that is shorter than the average heart rate, the reconstruction time may be further adjusted to avoid using projection or view data that overlaps a preceding or following PVC/R wave. The method may utilize a combination of the above factors when determining the reconstruction time.

At 330, method 300 reconstructs images based on the determined reconstruction times. By reconstructing images corresponding to the determined reconstruction times, the images are inherently well-registered. In this way, post-processing of the images to register the images to each other or otherwise correct for motion between the images may not be necessary. It should be understood that the images may be reconstructed using any suitable image reconstruction algorithm, including but not limited to filtered backprojection (FBP).

At 335, method 300 outputs the images. Outputting the images may comprise one or more of, as non-limiting examples, outputting the images to a display device (e.g., display device 232) for display to a user, saving the images to a local storage device (e.g., mass storage 218), and transmitting the images to a picture archiving and communication system (e.g., PACS 224), depending on whether the images are ready for review and/or additional processing. Method 300 then ends.

Figure 4:
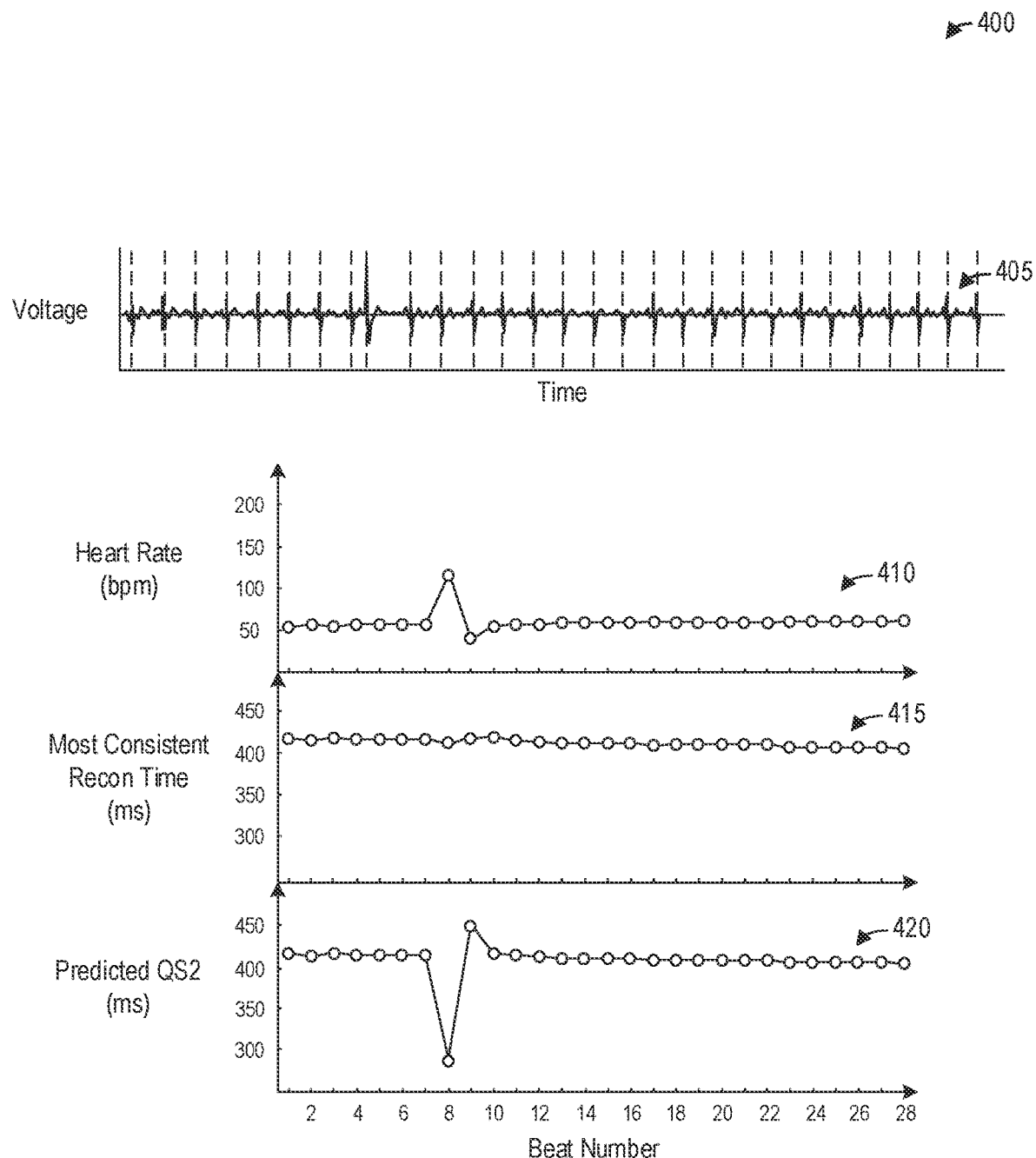
FIG. 4 shows a set of graphs illustrating an example method for imaging an organ over time according to an embodiment of the invention.

FIG. 4 shows a set of graphs 400 illustrating an example embodiment of the method 300 described hereinabove. The set of graphs 400 includes an ECG 405 of a patient with R-waves indicated by vertical dashed lines. The ECG 405 may be acquired while a set of CT scans is performed, wherein each CT scan acquires projection data between R-waves.

The set of graphs 400 further includes a plot 410 of the heart rate corresponding to the ECG 405. Each circle of the plot 410 corresponds to an instantaneous heart rate of the patient. Notably, the heart rate substantially increases from 58 beats per minute (bpm) at beat number seven to 118 bpm at beat number eight, with a compensatory heart rate of 41 bpm at beat number nine, before returning to a normal or regular heart rate of 57 bpm at beat number ten. Further, aside from the irregular heart rates at beats number eight and nine, the heart rate drifts from 57 bpm at beat number one to 63 bpm at beat number twenty-eight.

Previous approaches to image reconstruction for cardiac imaging merely use a constant or fixed time or a constant percentage of the RR interval after a previous R-wave for the reconstruction time. Such approaches will not account for the drift in heart rate noted above, and furthermore will not provide a good result for an image reconstructed with data between beats eight and nine. In contrast, by modeling the desired cardiac event to be imaged, such as the QS2 interval, as described hereinabove with regard to FIG. 3, consistent reconstructions can be obtained.

To that end, the set of graphs 400 further includes a plot 415 of the most consistent reconstruction time for each acquisition, and a plot 420 of the predicted QS2 for each acquisition. The duration of the total electromechanical systole is measured by the interval QS2 between the onset of the QRS in the ECG and the closure of the aortic valve, as determined by the onset of the second heart sound S2 which marks the end of the mechanical systole. It should be appreciated that the use of QS2 is exemplary only, and other events may be targeted for reconstruction as desired. The QS2 may be predicted based on a model relating cardiac events to heart rates as described hereinabove. Thus, the QS2 predictions depicted by plot 420 may be obtained based on the measured heart rates depicted by plot 410.

The most consistent reconstruction time may directly correspond to the predicted QS2, as illustrated by plot 415. However, the reconstruction time for beat numbers eight and nine may be adjusted due to the irregular heartbeats. For example, for beat number eight, the predicted QS2 is 292.2 milliseconds. Evidently, beat number eight does not go through a normal cardiac cycle, possibly due to a pre-ventricular contraction. To use the clean data just before PVC, the most consistent reconstruction time is 415.1 milliseconds. This reconstruction time is selected in order to perform the reconstruction as close as possible to the time of the prior normal beat (418.2 milliseconds) while also ensuring that the 240 degrees of scan data, acquired at 280 milliseconds per rotation, all comes before the PVC/R-wave at 508 milliseconds.

Meanwhile, for beat number nine, the predicted QS2 is 453.9 milliseconds. Since beat number nine is a compensatory beat, the end-systolic time will be similar to the neighboring normal beats, so the most consistent reconstruction time is determined to be 419.2 milliseconds, the average of the neighboring reconstruction times (418.2 milliseconds for the prior normal beat and 420.3 milliseconds for the subsequent normal beat).

Thus, the predicted end of electromechanical systole obtained based on a linear model may be used to determine the most consistent reconstruction time, with suitable corrections applied for irregular heartbeats.

Figure 5:
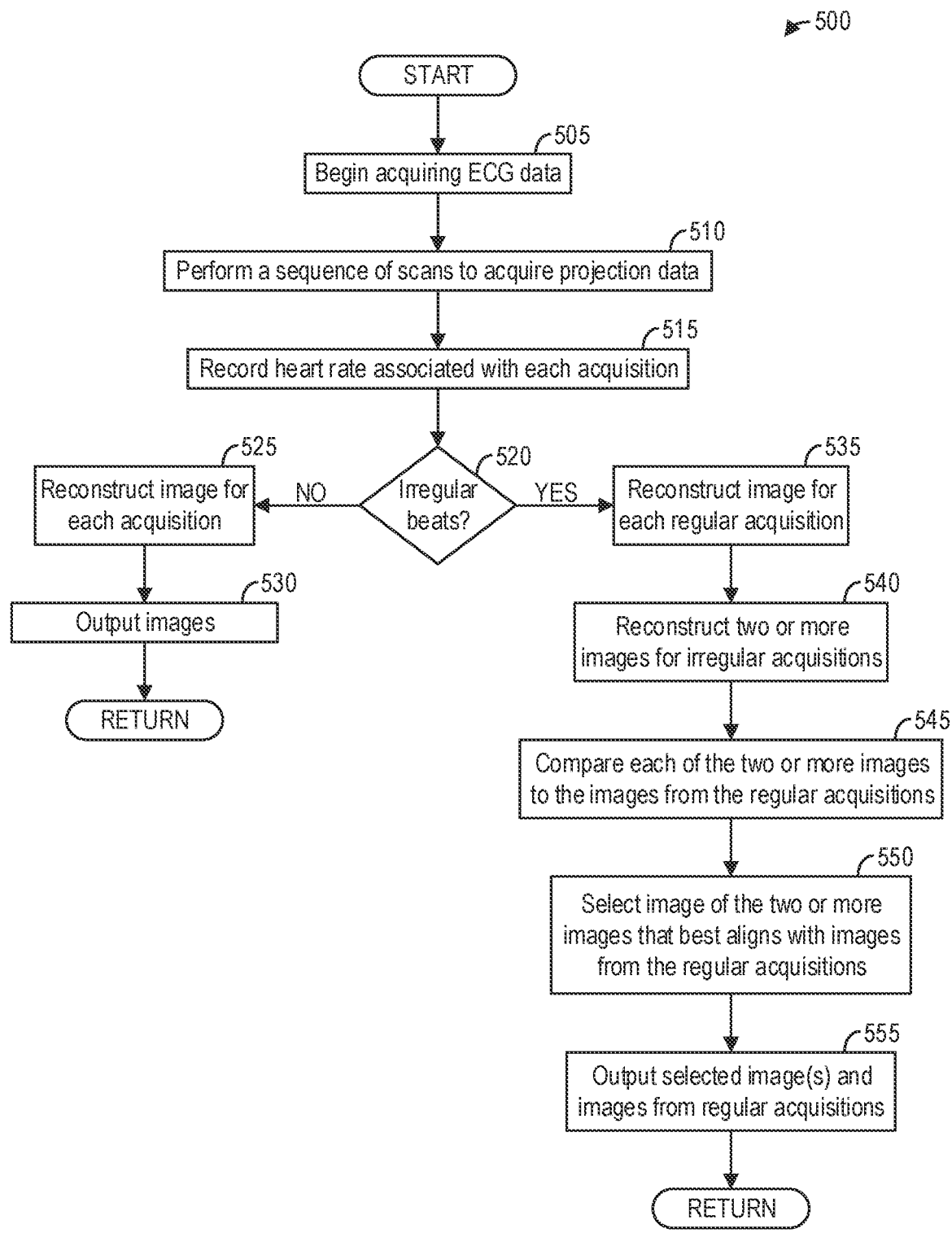
FIG. 5 shows a high-level flow chart illustrating another example method for consistently imaging an organ over time according to an embodiment of the invention.

FIG. 5 shows a high-level flow chart illustrating an example method 500 for consistently imaging an organ over time according to an embodiment. In particular, method 500 relates to adaptively searching for the best reconstruction time for reconstructions during cardiac cycles that are different from a mean or usual cardiac cycle. Method 500 is described with reference to the systems and components of FIGS. 1-2, though it should be understood that the method may be implemented with other systems and components without departing from the scope of the present disclosure. Method 500 may be implemented as executable instructions in the non-transitory memory of a computing device such as computer 216, for example.

Method 500 begins at 505. At 505, method 500 begins acquiring ECG data for a subject. For example, ECG data may be acquired via the ECG leads 235 of the ECG monitor 234 positioned on the subject 204. The ECG data or the ECG signal may be collected from the patient to synchronize the acquisition of imaging data with the quiescent period of cardiac motion.

At 510, method 500 performs a sequence of scans to acquire projection data. For example, method 500 may control the x-ray source 104 to administer x-rays to the subject 204 in the form of a fan or cone while CT projection data is acquired via the detectors 108 and the DAS 214. Method 500 may perform each scan to acquire data during a CT data acquisition window corresponding to the quiescent periods in the real-time phase of the cardiac cycle where the heart is relatively stationary.

At 515, method 500 records the heart rate associated with each acquisition. By using the ECG data, the instantaneous heart rate for each acquisition can be recorded. For example, method 500 may calculate the heart rate associated with each acquisition based on the R wave-to-R wave (RR) interval recorded by the ECG.

At 520, method 500 determines if irregular beats are present. An irregular heartbeat may be identified by determining if one or more of the measured heart rates deviates beyond a threshold range of the average of other measured heart rates, as a non-limiting example.

If no irregular beats are present ("NO"), method 500 proceeds to 525. At 525, method 500 reconstructs an image for each acquisition. The reconstruction times may be determined based on the model described hereinabove with regard to FIG. 3, as a non-limiting example. In other examples, a fixed time or percentage of the RR interval may be selected as the reconstruction time. At 530, method 500 outputs the reconstructed images. Outputting the images may comprise one or more of, as non-limiting examples, outputting the images to a display device (e.g., display device 232) for display to a user, saving the images to a local storage device (e.g., mass storage 218), and transmitting the images to a picture archiving and communication system (e.g., PACS 224), depending on whether the images are ready for review and/or additional processing. Method 500 then returns.

However, referring again to 520, if irregular beats are present ("YES"), method 500 proceeds to 535. At 535, method 500 reconstructs an image for each regular acquisition, wherein a regular acquisition refers to an acquisition corresponding to a regular heartbeat (i.e., acquisitions with instantaneous heart rates measured within a threshold range of the average heart rate acquired). The reconstruction times for such reconstructions may be determined as described hereinabove with regard to FIG. 3. For example, a model relating the cardiac event to be imaged to the measured heart rate may be used to determine the optimal reconstruction time.

Further, at 540, method 500 reconstructs two or more images for each irregular acquisition. Each of the two or more images may be reconstructed with different reconstruction times but from the same set of projection data acquired during the acquisition. It should be appreciated that a larger acquisition window may be used during the scans at 510 in order to obtain sufficient data for multiple reconstructions.

Thus, for acquisitions during heart rates that are different beyond an absolute or relative threshold from neighboring heart rates, two or more reconstructions are performed and the reconstruction that best aligns or registers with the neighboring frames is used. To that end, at 545, method 500 compares each of the two or more images to the images from the neighboring regular acquisitions. As an illustrative example, the images may be compared by subtracting each of the two or more images from one or more of the neighboring regular images, and determining which of the two or more images is most similar to the one or more neighboring regular images based on the resulting difference image.

It should be appreciated that any suitable method may be used to determine which reconstruction is most similar to an average or representative reconstruction. For example, when the scan range is for the same anatomical region for the different reconstructions, relative distances between each of a number of landmarks derived from segmentation of the cardiac anatomy may be subtracted from the relative distances between those same landmarks on a representative reconstruction, then squared and summed. Alternatively, considering the CT number along various lines through the heart, in any or all of a left/right direction, an anterior/posterior direction, and a superior/inferior direction, the absolute value of a spatial derivative may be computed to determine the location of edges, optionally including a threshold that must be exceeded to identify an edge or surface between different materials, with an alignment metric derived by squaring and summing the differences in distances between corresponding edges over multiple lines.

As another example, when the scan regions are next to each other, the same metrics may be derived from corresponding or neighboring image slices at the edges of the volumes, with the comparisons being limited measurements within the axial planes.

As yet another example, a mutual information metric may be computed, which is maximized when images are geometrically aligned. Mutual information or relative entropy measures the statistical dependence between two random variables or the amount of information that one variable contains about the other. As an example, the mutual information of the image intensity values of corresponding voxel pairs is maximal if the images are geometrically aligned. A mask or segmentation of the cardiac region may be applied before the mutual information is computed, to focus the registration metric on the heart and not on the structures of the lungs or chest wall. The mutual information may be computed for the entire volume, or, when aligning neighboring subvolumes, for corresponding or neighboring image slices.

The various metrics discussed hereinabove for comparing images may be referred to herein as a similarity metric. Comparing each of the two or more images to the images from the neighboring regular acquisitions therefore comprises calculating a similarity metric for each image of the two or more images.

Continuing at 550, method 500 selects an image of the two or more images that best aligns with the images from the regular acquisitions. The image of the two or more images that best aligns with the images from the regular acquisitions comprises the image for which the similarity metric computed at 545 is the highest.

At 555, method 500 outputs the selected image(s) and the images from the regular acquisitions. As described above, outputting the images may comprise one or more of, as non-limiting examples, outputting the images to a display device (e.g., display device 232) for display to a user, saving the images to a local storage device (e.g., mass storage 218), and transmitting the images to a picture archiving and communication system (e.g., PACS 224), depending on whether the images are ready for review and/or additional processing. Method 500 then ends.

Thus, the present disclosure provides systems and methods for adaptively searching for the best reconstruction time for reconstructions during cardiac cycles that are different from a mean or usual cardiac cycle. Further, in some examples, a post-processing registration algorithm generates a metric on the success of the registration between images. For those frames that are not well registered, alternate reconstructions may be generated and the reconstruction that is best registered, either before or after the registration process, may be used instead of the original frame.

Although the method 500 is described with regard to imaging a portion of a heart at a consistent point in the cardiac cycle, it should be appreciated that method 500 may be utilized for other cardiac imaging scenarios. For example, some CT scanners do not have sufficient coverage to scan the entire heart; such scanners typically take data from different time intervals, typically different heartbeats, to generate images of portions of the heart at each of those time intervals. Previous approaches create the image volumes at the same phase of the corresponding cardiac cycle, or at the same time after the R-wave. The method 500 may thus be used to obtain consistent image reconstructions for each portion of the heart, thereby minimizing visible shifts within the heart (or another object being imaged) at the shifts between separately acquired image volumes. The method described hereinabove with regard to FIG. 3 also provides for the determination of the best or most consistent reconstruction interval for each region of the heart.

A technical effect of the disclosure is the reconstruction of a plurality of well-registered images. Another technical effect of the disclosure is the calculation of an optimal reconstruction time based on a heart rate. Yet another technical effect of the disclosure is the display of a series of images that are aligned or registered with each other even if one of the images is acquired during an irregular cardiac cycle.

In one embodiment, a method comprises reconstructing an image from projection data acquired during a scan with a reconstruction time determined based on a model relating a timing of an event to be imaged to a heart rate measured during the scan.

In a first example of the method, the method further comprises acquiring electrocardiogram (ECG) data during the scan, wherein the heart rate is measured based on the ECG data. In a second example of the method optionally including the first example, the reconstruction time is further determined based on presence of an irregular heartbeat identified in the ECG data. In a third example of the method optionally including one or more of the first and second examples, the reconstruction time is adjusted to avoid using views in the projection data corresponding to an R-wave of the ECG data during the reconstruction. In a fourth example of the method optionally including one or more of the first through third examples, responsive to the presence of the irregular heartbeat, the reconstruction time is determined based on reconstruction times corresponding to neighboring regular heartbeats. In a fifth example of the method optionally including one or more of the first through fourth examples, the scan is synchronized with the ECG data to acquire the projection data between R-waves of the ECG data. In a sixth example of the method optionally including one or more of the first through fifth examples, the event comprises an end of electromechanical systole. In a seventh example of the method optionally including one or more of the first through sixth examples, the model is adapted to a subject being imaged.

In another embodiment, a method comprises: performing a plurality of scans to acquire projection data; recording a heart rate associated with each scan; responsive to at least one heart rate of a first scan in the plurality of scans beyond a threshold from neighboring heart rates, reconstructing at least two images from projection data acquired during the first scan; and outputting one image of the at least two images that more closely aligns with an image reconstructed from projection data acquired during a second scan with a heart rate within the threshold. In another representation, a method comprises: performing a plurality of scans to acquire projection data; recording a heart rate associated with each scan; responsive to at least one heart rate of a first scan in the plurality of scans beyond a threshold from neighboring heart rates, reconstructing at least two images from projection data acquired during the first scan; calculating a similarity metric for each image of the at least two images and an image reconstructed from projection data acquired during a second scan with a heart rate within the threshold; and outputting one image of the at least two images based on the similarity metric.

In a first example of the method, the method further comprises outputting the image reconstructed from the projection data acquired during the second scan. In a second example of the method optionally including the first example, the method further comprises acquiring electrocardiogram (ECG) data while performing the plurality of scans, wherein the heart rate associated with each scan is determined from the ECG data. In a third example of the method optionally including one or more of the first and second examples, each scan of the plurality of scans is performed between R-waves of the ECG data. In a fourth example of the method optionally including one or more of the first through third examples, the at least two images are reconstructed with different reconstruction times. In a fifth example of the method optionally including one or more of the first through fourth examples, calculating the similarity metric for each image of the at least two images comprises comparing each image of the at least two images to the image to determine which of the at least two images more closely aligns with the image. In a sixth example of the method optionally including one or more of the first through fifth examples, each of the at least two images corresponds to a first portion of an organ being imaged, and wherein the image corresponds to a second portion of an organ being imaged.

In yet another embodiment, a system comprises: a gantry, the gantry defining a bore; an x-ray source that emits a beam of x-rays toward an object to be imaged, the x-ray source positioned on the gantry; a detector that receives the x-rays attenuated by the object, the detector positioned on the gantry; a data acquisition system (DAS) operably connected to the detector; and a computer operably connected to the DAS and the x-ray source, the computer configured with instructions in non-transitory memory that when executed cause the computer to: reconstruct an image from projection data acquired via the DAS during a scan of the object with a reconstruction time determined based on a model relating a timing of an event to be imaged to a heart rate measured during the scan.

In a first example of the system, the system further comprises an electrocardiogram (ECG) monitor communicatively coupled to the computer, wherein the heart rate is measured based on data received from the ECG monitor. In a second example of the system optionally including the first example, the reconstruction time is further determined based on presence of an irregular heartbeat identified in the data received from the ECG monitor. In a third example of the system optionally including one or more of the first and second examples, the reconstruction time is adjusted to avoid using views in the projection data corresponding to an R-wave of the data received from the ECG monitor during the reconstruction. In a fourth example of the system optionally including one or more of the first through third examples, responsive to the presence of the irregular heartbeat, the reconstruction time is determined based on reconstruction times corresponding to neighboring regular heartbeats.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   acquiring, via an electrocardiogram (ECG) monitor, ECG data during a computed tomography (CT) scan, wherein a heart rate of a patient undergoing the CT scan is measured based on the ECG data;
   acquiring image projection data of the patient undergoing the CT scan; and
   reconstructing, using an image reconstructor, an image from the image projection data acquired during the CT scan with a reconstruction time determined based on a model relating a timing of an event to be imaged to the heart rate measured during the CT scan, wherein the reconstruction time is further determined based on presence of an irregular heartbeat identified in the ECG data, and wherein, responsive to the presence of the irregular heartbeat, the reconstruction time is determined based on reconstruction times corresponding to neighboring regular heartbeats.

2. The method of claim 1, wherein the reconstruction time is adjusted to avoid using views in the projection data corresponding to an R-wave of the ECG data during the reconstruction.

3. The method of claim 1, wherein the scan is synchronized with the ECG data to acquire the projection data between R-waves of the ECG data.

4. The method of claim 1, wherein the event comprises an end of electromechanical systole.

5. The method of claim 1, wherein the model is adapted to a subject being imaged.

6. A system, comprising:
   a gantry, the gantry defining a bore;
   an x-ray source that emits a beam of x-rays toward a patient to be imaged, the x-ray source positioned on the gantry;
   a detector that receives the x-rays attenuated by the patient, the detector positioned on the gantry;
   an electrocardiogram (ECG) monitor communicatively coupled to the computer, wherein a heart rate of the patient undergoing a CT scan is measured based on data received from the ECG monitor;
   a data acquisition system (DAS) operably connected to the detector; and
   a computer operably connected to the DAS and the x-ray source, the computer configured with instructions in non-transitory memory that when executed cause the computer to:
   acquire image projection data of the patient undergoing the CT scan; and
   reconstruct an image from projection data acquired via the DAS during the CT scan of the patient with a reconstruction time determined based on a model relating a timing of an event to be imaged to the heart rate measured during the CT scan, wherein the reconstruction time is further determined based on presence of an irregular heartbeat identified in the data received from the ECG monitor, and wherein, responsive to the presence of the irregular heartbeat, the reconstruction time is determined based on reconstruction times corresponding to neighboring regular heartbeats.

7. The system of claim 6, wherein the reconstruction time is adjusted to avoid using views in the projection data corresponding to an R-wave of the data received from the ECG monitor during the reconstruction.

* * * * *